United States Patent
Auchter et al.

(10) Patent No.: US 8,256,330 B2
(45) Date of Patent: Sep. 4, 2012

(54) GUARDED SURGICAL KNIFE HANDLE

(75) Inventors: Gregory Allen Auchter, Reading, PA (US); Randal Lee Berardi, Ephrata, PA (US); Edwin Warren Blatt, Denver, PA (US); Jeffrey Kirk Landis, Birdsboro, PA (US); David Robert Schiff, Highland Park, NJ (US); Seth McCue GaleWyrick, Asheville, NC (US)

(73) Assignee: Alcon Research, Ltd., Fort Worth, TX (US)

(*) Notice: Subject to any disclaimer, the term of this patent is extended or adjusted under 35 U.S.C. 154(b) by 403 days.

(21) Appl. No.: 12/620,251

(22) Filed: Nov. 17, 2009

(65) Prior Publication Data

US 2010/0125290 A1    May 20, 2010

Related U.S. Application Data

(60) Provisional application No. 61/116,479, filed on Nov. 20, 2008.

(51) Int. Cl.
*A61B 17/32* (2006.01)
*B26B 3/00* (2006.01)

(52) U.S. Cl. ........ 83/13; 30/2; 30/151; 30/329; 606/167
(58) Field of Classification Search ................ 30/2, 151, 30/162, 163, 335, 329, 339; 606/166, 167, 606/181, 182; 83/13
See application file for complete search history.

(56) References Cited

U.S. PATENT DOCUMENTS

| | | |
|---|---|---|
| 1,735,271 A | 11/1929 | Groff |
| 2,512,237 A | 6/1950 | Mravik |
| 3,748,736 A | 7/1973 | Eisen |
| 3,793,726 A | 2/1974 | Schrank |
| 3,905,101 A | 9/1975 | Shepherd |
| 3,906,626 A | 9/1975 | Riuli |
| 4,071,952 A | 2/1978 | Meshulam et al. |
| 4,165,745 A | 8/1979 | Heifetz |
| 4,414,974 A | 11/1983 | Dotson et al. |
| 4,523,379 A | 6/1985 | Osterhout et al. |
| 4,552,146 A | 11/1985 | Jensen et al. |

(Continued)

FOREIGN PATENT DOCUMENTS

DE    3722899 A1    1/1989

(Continued)

OTHER PUBLICATIONS

International Searching Authority, PCT International Preliminary Examination Report, PCT/GB01/01561, May 13, 2002, 2 pages.

(Continued)

*Primary Examiner* — Phong Nguyen
(74) *Attorney, Agent, or Firm* — Darien Reddick

(57) ABSTRACT

A guarded surgical knife handle includes a lower handle portion, an upper handle postion, and a button. The lower handle portion includes a blade holder, a proximal pair of lateral shelves, and a distal pair of lateral shelves. The upper handle portion includes a guard portion, a proximal post between the proximal pair of shelves with a first widened post portion wider than the lateral spacing between the shelves, and a distal post between the distal pair of shelves with a second widened post portion wider than the lateral spacing between the shelves. The button has a button waist narrower than the second lateral spacing and a widened button portion below the button waist wider than the second lateral spacing. A bias member connected to the button and at least one of the handle portions provides an upward force on the button.

26 Claims, 3 Drawing Sheets

U.S. PATENT DOCUMENTS

| | | |
|---|---|---|
| 4,576,164 A | 3/1986 | Richeson |
| 4,635,914 A | 1/1987 | Kabanek |
| 4,660,287 A | 4/1987 | Decker |
| 4,674,500 A | 6/1987 | DeSatnick |
| 4,733,662 A | 3/1988 | DeSatnick et al. |
| 4,759,363 A | 7/1988 | Jensen |
| 4,768,509 A | 9/1988 | Grosvenor et al. |
| 4,790,312 A | 12/1988 | Capuano, Sr. et al. |
| 4,896,983 A | 1/1990 | Im et al. |
| 4,903,390 A | 2/1990 | Vidal et al. |
| 5,026,386 A | 6/1991 | Michelson |
| 5,059,210 A | 10/1991 | Clark et al. |
| 5,092,852 A | 3/1992 | Poling |
| 5,116,351 A | 5/1992 | Frassetti |
| 5,201,748 A | 4/1993 | Newman et al. |
| 5,207,696 A | 5/1993 | Matwijcow |
| 5,234,436 A | 8/1993 | Eaton et al. |
| 5,250,063 A | 10/1993 | Abidin et al. |
| 5,250,064 A | 10/1993 | Schneider |
| 5,254,128 A | 10/1993 | Mesa |
| 5,275,606 A | 1/1994 | Abidin et al. |
| 5,292,329 A | 3/1994 | Werner |
| 5,299,357 A | 4/1994 | Wonderley et al. |
| 5,309,641 A | 5/1994 | Wonderley et al. |
| 5,330,492 A | 7/1994 | Haugen |
| 5,330,494 A | 7/1994 | van der Westhuizen et al. |
| 5,352,220 A | 10/1994 | Abidin et al. |
| 5,391,177 A | 2/1995 | Schwartz |
| 5,403,337 A | 4/1995 | Platts |
| 5,411,512 A | 5/1995 | Abidin et al. |
| 5,417,704 A | 5/1995 | Wonderley |
| 5,475,925 A | 12/1995 | Newman et al. |
| 5,496,340 A | 3/1996 | Abidin et al. |
| 5,556,409 A | 9/1996 | Haining |
| 5,569,281 A | 10/1996 | Abidin et al. |
| 5,571,127 A | 11/1996 | DeCampli |
| 5,571,128 A | 11/1996 | Shapiro |
| 5,620,454 A | 4/1997 | Pierce et al. |
| 5,683,407 A | 11/1997 | Jolly et al. |
| 5,702,369 A | 12/1997 | Mercereau |
| 5,741,289 A | 4/1998 | Jolly et al. |
| 5,830,226 A | 11/1998 | Webb et al. |
| 5,908,432 A | 6/1999 | Pan |
| 5,919,201 A | 7/1999 | Carter et al. |
| 5,941,892 A | 8/1999 | Cohn et al. |
| 6,022,364 A | 2/2000 | Flumene et al. |
| 6,503,262 B1 | 1/2003 | Edens |
| 6,569,175 B1 | 5/2003 | Robinson |
| 6,623,499 B1 | 9/2003 | Andreini et al. |
| 6,626,925 B2 | 9/2003 | Newman et al. |
| D496,730 S | 9/2004 | Morawski |
| 6,884,240 B1 | 4/2005 | Dykes |
| 7,022,128 B2 | 4/2006 | Morawski et al. |
| 7,087,067 B2 | 8/2006 | Kehr et al. |
| 7,101,382 B2 | 9/2006 | George et al. |
| 7,153,317 B2 | 12/2006 | Kanodia et al. |
| 7,159,713 B1 | 1/2007 | Austria |
| 7,175,643 B2 | 2/2007 | Shi |
| 7,387,637 B2 | 6/2008 | Morawski et al. |
| 2002/0143352 A1 | 10/2002 | Newman et al. |
| 2003/0074013 A1 | 4/2003 | Schooler et al. |
| 2003/0225428 A1 | 12/2003 | Saito et al. |
| 2004/0098004 A1 | 5/2004 | George et al. |
| 2004/0111106 A1 | 6/2004 | Iske et al. |
| 2004/0158269 A1 | 8/2004 | Holman |
| 2004/0186496 A1 | 9/2004 | Sandel et al. |
| 2004/0215174 A1 | 10/2004 | Morawski et al. |
| 2004/0243161 A1 | 12/2004 | Kanodia et al. |
| 2005/0015104 A1 | 1/2005 | Morawski et al. |
| 2005/0119680 A1 | 6/2005 | Dykes |
| 2005/0267502 A1 | 12/2005 | Hochman |
| 2006/0085019 A1 | 4/2006 | Cote et al. |
| 2006/0100650 A1 | 5/2006 | Kiehne |
| 2006/0241664 A1 | 10/2006 | Lam |
| 2007/0255298 A1 | 11/2007 | Djordjevic et al. |
| 2008/0058843 A1 | 3/2008 | Morawski et al. |
| 2008/0058844 A1 | 3/2008 | Morawski et al. |
| 2008/0141539 A1 | 6/2008 | Co |

FOREIGN PATENT DOCUMENTS

| | | |
|---|---|---|
| EP | 0162170 A1 | 11/1985 |
| EP | 0555196 A1 | 8/1993 |
| EP | 0583992 A1 | 2/1994 |
| EP | 0709064 A1 | 5/1996 |
| EP | 0727186 A2 | 8/1996 |
| EP | 0988832 A2 | 3/2000 |
| WO | WO 92/15254 A1 | 2/1992 |
| WO | WO 93/11916 A1 | 6/1993 |
| WO | WO 93/21837 A1 | 11/1993 |
| WO | WO 93/24064 A1 | 12/1993 |
| WO | WO 95/15723 A1 | 6/1995 |
| WO | WO 96/01080 A1 | 1/1996 |
| WO | WO 97/37599 A1 | 10/1997 |
| WO | WO 01/74257 A1 | 10/2001 |
| WO | WO 03/099145 A1 | 12/2003 |
| WO | WO 2004/026151 A1 | 4/2004 |
| WO | WO 2005/089202 A2 | 9/2005 |

OTHER PUBLICATIONS

International Searching Authority, PCT International Preliminary Examination Report, PCT/AU03/001187, Jan. 17, 2005, 8 pages.

FIG. 3 (500)

START

Depress button (502)

Slide button between distal shelves in proximal direction (504)

Release button (506)

Depress button (508)

Slide button between distal shelves in distal direction (510)

Release button (512)

END

GUARDED SURGICAL KNIFE HANDLE

RELATED APPLICATIONS

This application claims priority to U.S. provisional application Ser. No. 61/116,479, filed on Nov. 20, 2008, the contents which are incorporated herein by reference.

SUMMARY

In particular embodiments of the present invention, a guarded surgical knife handle includes a lower handle portion, an upper handle portion, and a button. The lower handle portion includes a blade holder, a proximal pair of lateral shelves, and a distal pair of lateral shelves. The upper handle portion includes a guard portion, a proximal post between the proximal pair of shelves with a first widened post portion wider than the lateral spacing between the shelves, and a distal post between the distal pair of shelves with a second widened post portion wider than the lateral spacing between the shelves. The button has a button waist narrower than the second lateral spacing and a widened button portion below the button waist wider than the second lateral spacing. A bias member connected to the button and at least one of the handle portions provides an upward force on the button. Further understanding of various aspects of the invention can be obtained by reference to the following detailed description in conjunction with the drawings, which are discussed briefly below.

In other embodiments of the present invention, a method of guarding a surgical knife includes providing a guarded surgical knife handle in an unguarded position, wherein a button is positioned with a widened button portion against a proximal end of a distal pair of lateral shelves. The method further includes depressing the button, sliding the button longitudinally between the distal pair of shelves while the button is depressed to slide the upper handle portion into a guarded position, and releasing the button after the button passes a distal end of the distal pair of shelves.

BRIEF DESCRIPTION OF THE DRAWINGS

FIG. 3 is a flow chart showing an example method of unguarding and guarding a surgical knife according to a particular embodiment of the present invention.

DETAILED DESCRIPTION

Particular embodiments of the present invention provide a guarded surgical knife handle including an upper handle portion slidably attached to a lower handle portion. In certain embodiments, a button is depressed to slide the upper handle portion between an unguarded and a guarded position, and a bias member provides an upward force, which allows the button to be held in place with respect to the upper handle portion. Further description of various preferred exemplary embodiments in conjunction with the figures is provided below.

For purposes of this description, the following conventions are employed in naming various locations of the guarded surgical knife handle. "Longitudinal" describes a direction generally along an axis between one end of the guarded surgical knife that holds a blade in proximity to a patient and the opposite end near the surgeon. "Proximal" describes a location relatively closer to the surgeon than the patient in the longitudinal direction; conversely, "distal" refers to a location that is closer to the patient. "Upper," "lower," "top," and "bottom" describe locations in terms of the orientation of the guarded surgical knife handle as it is held by a surgeon to perform incisions on a patient. "Vertical" describes a direction generally along an axis between the top and bottom of the guarded surgical knife handle, while "height" measures a distance in a vertical direction. "Lateral" describes a direction generally along an axis perpendicular to the longitudinal and vertical directions, corresponding generally to left and right directions from the surgeon's perspective.

Figure 1:
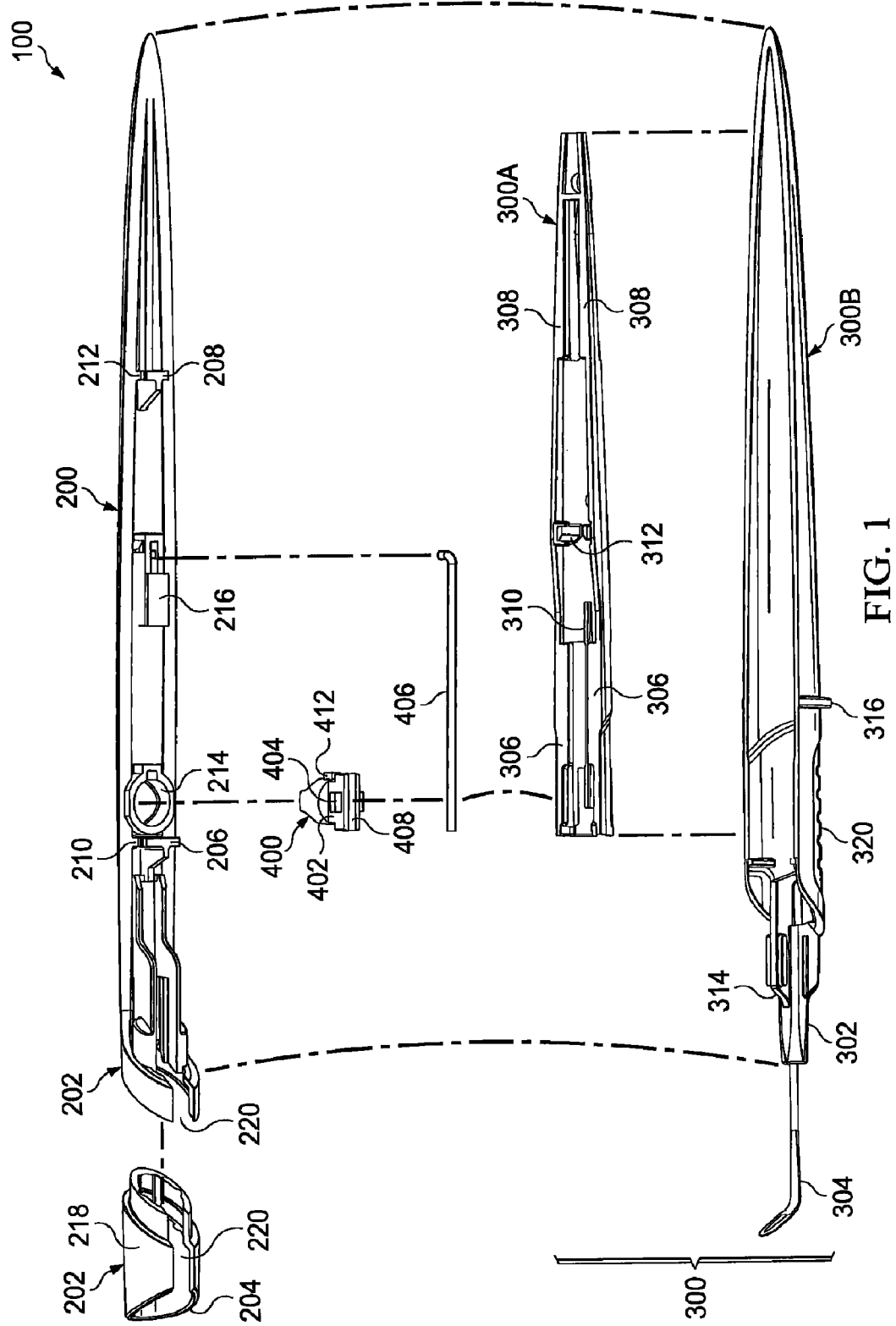
FIG. 1 is a disassembled view of a guarded surgical knife handle according to a particular embodiment of the present invention.
Figure 2:
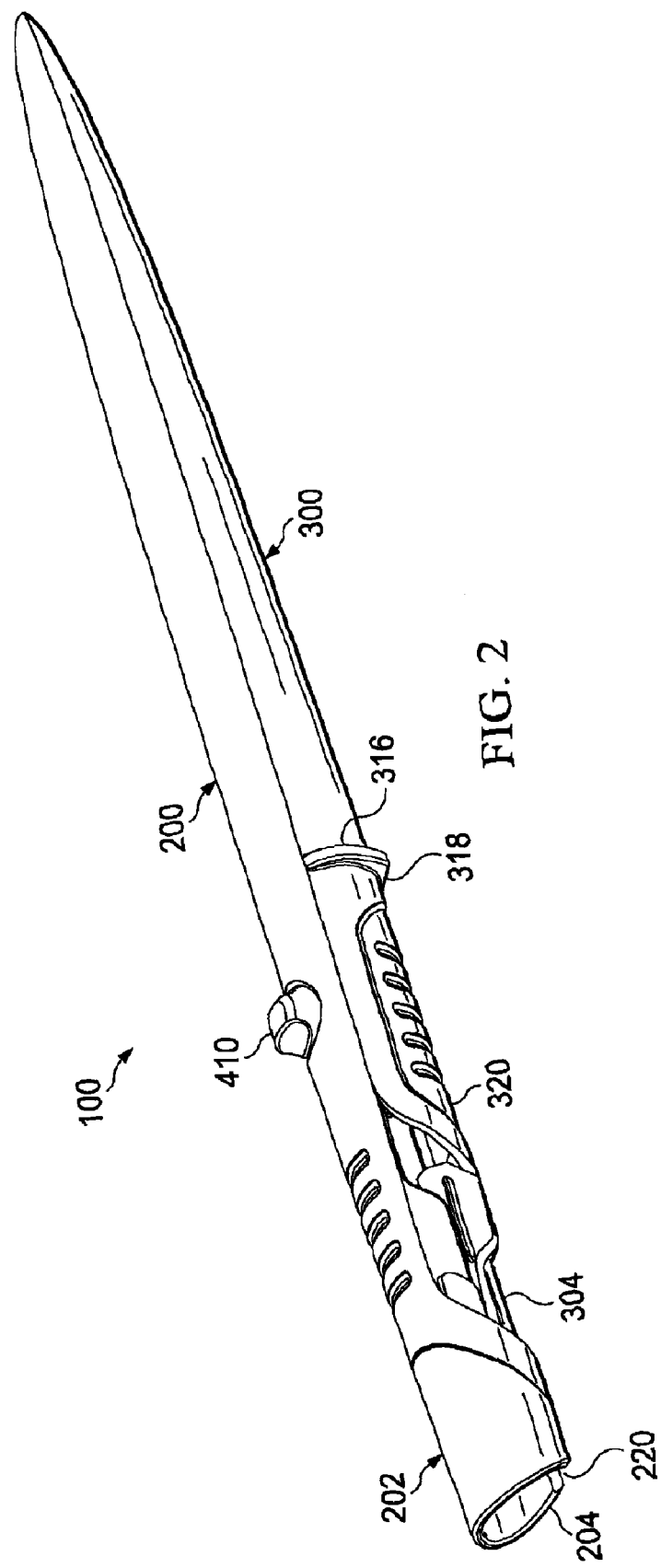
FIG. 2 illustrates the guarded surgical knife handle in a guarded position.

FIG. 1 illustrates a disassembled view of various components of a guarded surgical knife handle 100 according to a particular embodiment of the present invention, while FIG. 2 illustrates the assembled guarded surgical knife 100 in a guarded position. In the depicted embodiment, the guarded surgical knife handle 100 includes an upper handle portion 200 and a lower handle portion 300 that includes an insert portion 300A and an outer portion 300B. The insert portion 300A and the outer portion 300B may be securely attached to one another, such as by sonic welding, and in alternative embodiments, the lower handle portion 300 may also be formed as a single piece. The upper handle portion includes a guard portion 202, which is depicted as assembled from two pieces but which may also be formed from a single piece. The guard portion 202 includes an open distal end 204. The lower handle portion 300 includes a blade holder 302 adapted to hold a blade 304. The blade 304 may be any sort of blade suitable for surgical incisions and may have a straight or curved edge.

In various embodiments of the present invention, the blade 304 may be straight or may be inclined at a particular height and angle (as depicted in FIG. 1), and the guarded surgical knife handle 100 may have colored portions according to a predetermined color code to indicate the type of blade for the guarded surgical knife handle 100. The guard portion 202 is sized appropriately for the particular type of blade 304, which may be done, for example, by increasing the height of the guard portion 202 at the open distal end 204 or by selecting a sufficiently large uniform height and/or width of the guard portion 202 along its entire length. The relative height of the blade holder 302 above a bottom of the lower handle portion 300 may be selected to facilitate use of the blade 304 during surgery and to easily fit the guard portion 202 around the blade 304. For example, a blade holder 302 used to hold a straight blade might hold the point of blade at a height approximately in the middle of guarded surgical knife, while a blade holder 302 for a blade with a larger height might be placed at the bottom of the lower handle portion 300.

The guard portion 202 may include also additional safety features to further reduce the likelihood of inadvertent contact with the blade 304. For example, if guard portion 202 has a height and/or width sufficiently large to admit a finger at the open distal end 204, the guard portion 202 may include narrowing features such as internal ribs (not shown) to prevent the finger from entering the guard portion 202. The guarded surgical knife handle 100 may also include features to prevent the guard from being displaced so as to contact the blade 304. In the depicted embodiment, the lower handle portion 300 includes a blade contact stop 314. The blade contact stop 314 includes a widened portion that fits between ribs within the guard portion 202 (not shown) to prevent the guard portion 202 from being displaced downward toward the blade 304.

Other features that stop movement of the guard in a downward direction could also be used for the blade contact stop 314.

The guard portion 202 may be advantageously configured to allow the surgeon to more easily visualize the blade 304. For example, the guard portion 202 may be formed partially or entirely from a transparent material, so that the surgeon can see the blade in both the guarded and unguarded positions. The guard portion 202 may also be configured to move slightly downward when it is slid into an unguarded position, so that the surgeon may more easily see the blade 304 around the guard portion 202.

The upper handle portion 200 and the lower handle portion are slidably mounted to one another, and the details of the connection between the components are as follows. The upper handle portion 200 includes a distal post 206 and a proximal post 208, while the lower handle portion 300 includes distal lateral shelves 306 and proximal lateral shelves 308, each separated by a respective lateral spacing. The distal post 206 and proximal post 208 include widened post portions 210 and 212, respectively. When the guarded surgical knife handle 100 is assembled, the distal post 206 and proximal post 208 fit between the distal lateral shelves 306 and proximal lateral shelves 308, respectively. The widened post portions 210 and 212 are each wider than the lateral spacing of the respective lateral shelves 306 and 308, which is to say that the widened post portions 210 and 212 each extend beyond the lateral space between the respective lateral shelves 306 or 308 in at least one lateral direction. Thus, the posts 206 and 208 fit slidably between the respective lateral shelves 306 and 308, while the upper handle portion 200 and lower handle portion 300 are held together by the widened post portions 210 and 212.

A button 400 is also provided in the guarded surgical knife handle 100. The button 400 fits within a button hole 214 extending through an upper surface of the upper handle portion 200. The button 400 has a waist 402 narrower than the lateral spacing of the distal shelves 306, allowing the button waist 402 to fit between the distal shelves 306. The button also includes a widened button portion 404 that is wider than the lateral spacing of the distal shelves 306, which is to say that the widened button portion 404 extends beyond the lateral space between the distal shelves 306 in at least one lateral direction so that it cannot fit between the distal shelves 306.

A bias member 406 is connected to the button 400 and at least one of the upper handle portion 200 and the lower handle portion 200, such as by connecting the bias member 406 to a bias member base 216. The bias member 406 holds the button 400 in place when the button 400 is not depressed. When the button 400 is depressed, the bias member 406 provides an upward force on the button 400. In the depicted embodiment, the bias member 406 is a cantilevered pin that fits snugly within a bottom groove 408 on the button 400. However, any suitable method for attaching the bias member 406 to the button 400 may also be used.

In operation, the button 400 is used to slide the upper handle portion 200 between a guarded position and an unguarded position. In the guarded position, which is illustrated in FIG. 2, the button 400 is past a distal end of the distal lateral shelves 306. The bias member 406 holds the button 400 in an upward position so that the widened button portion 404 is level with the distal lateral shelves 306, which in turn prevents the upper handle portion 200 from sliding proximally. The detailed operation of unguarding and guarding the blade 304 (starting from the guarded position illustrated in FIG. 2) will explained in conjunction with the flow chart 500 of FIG. 3 along with descriptions of additional features of FIGS. 1 and 2 having functions that are more easily understood in the context of the unguarding and guarding operation.

To move the upper handle portion into the unguarded position, the button 400 is depressed at step 502 so that the button waist 402 is level with the distal shelves 306, and the button 400 is then slid between the distal shelves 306 in the proximal direction at step 504. The button 400 may include a rounded tab 410 that may facilitate depressing and sliding the button 400. In particular embodiments, the button 400 includes an alignment feature 412 that fits into a complementary receptacle in the button hole 214 to prevent the button 400 from rotating when depressed. In order to facilitate alignment of the button waist 402 with the distal shelves 306 when the button 400 is depressed, a button stop 310 may be included to restrict downward movement of the button 400 when the button waist 402 is at the height of the distal shelves 306. In the depicted embodiment, the button stop 310 is a pair of rails running beneath the distal shelves 306. The widened button portion 404 is wider than the lateral spacing between the rails so that the button stop 310 halts the button 400 when the widened button portion 404 reaches the rails.

After the button 400 is slid between the distal shelves 306 and past a proximal end of the distal shelves 306, the button 400 is released at step 506. The bias member 406 pushes the button 400 up so that the widened button portion 404 is positioned at the level of the distal shelves 206, preventing the upper handle portion 200 from moving distally. Thus, the upper handle portion 200 is securely held in the unguarded position.

In particular embodiments, the guard portion 202 has an underside 218 wrapping under the blade 304, which may include a channel 220 sized to fit around the blade holder 302. When the guard portion reaches the unguarded position, the underside 218 contacts a distal edge of the lower handle portion 300, stopping the proximal motion of the upper handle portion 200. Hitting the distal edge of the lower handle portion 200 may provide tactile feedback to the surgeon that the guard portion is in the unguarded position, so that the button 400 can be released.

To move the upper handle portion to the guarded position, the button 400 is depressed at step 508 and slid between the distal shelves 306 in the distal direction at step 510. Again, the button 400 is released after it is slid past the end of the distal shelves 306 at step 512, and the bias member 406 pushes the button 400 upward to rest behind the distal end of the distal shelves 306. A retention stop 312 may be used to restrict the longitudinal motion of the upper handle portion 200 so that the upper handle portion 200 does not slide off of the lower handle portion 300 when it is moved distally. In the depicted embodiment, the retention stop 312 includes two tension ribs. The guarded surgical knife handle 100 is assembled by placing the distal post 206 and proximal post 208 into spaces distal to the distal shelves 306 and proximal shelves 306, respectively. The upper handle portion 200 is then slid in the proximal direction, causing the bias member base 216 to displace the tension ribs of the retention stop 312. Once the bias member base 216 is past the tension ribs, the ribs return to their non-displaced position and interfere with the bias member base 216 to restrict the longitudinal motion of the upper handle portion 200 in a distal direction. Hitting the stop position can provide tactile feedback to the surgeon that the upper half portion 200 has reached the guarded position and that the button 400 can be released.

A grip feature 316 may be included to facilitate the guarding and unguarding process by allowing the surgeon to hold the guarded surgical knife handle 100 more securely while the button 400 is being depressed and slid. In the depicted embodiment, the grip feature 316 extends from a bottom surface of the lower handle half 200, allowing a secure finger hold against the grip feature 316. The grip feature 316 may advantageously include a flattened bottom surface 318 that prevents the guarded surgical knife handle 100 from rolling when it is set down on a level, flat surface. A textured grip surface 320 may also be placed adjacent to the grip feature 316 to make the surgeon's grip on the guarded surgical knife handle 320 more secure.

The present invention has been described by reference to certain preferred embodiments; however, it should be understood that it may be embodied in other specific forms or variations thereof without departing from its essential characteristics. The embodiments described above are therefore considered to be illustrative in all respects and not restrictive, the scope of the invention being indicated by the appended claims.

The invention claimed is:

1. A method of guarding a surgical blade comprising:
   providing, in an unguarded position, a guarded surgical knife handle comprising:
      a lower handle portion comprising a blade, a proximal pair of lateral shelves separated by a first lateral spacing, and a distal pair of lateral shelves separated by a second lateral spacing;
      an upper handle portion comprising a guard portion that is open at a distal end of the upper handle portion and sized to surround the blade, a proximal post extending downwardly between the proximal pair of shelves and having a first widened post portion below the proximal pair of shelves that is wider than the first lateral spacing, and a distal post extending downwardly between the distal pair of shelves and having a second widened post portion below the distal pair of shelves that is wider than the second lateral spacing;
      a button extending through a button hole in an upper surface of the upper handle portion, the button comprising a button waist narrower than the second lateral spacing and a widened button portion below the button waist wider than the second lateral spacing, wherein the button is positioned with the widened button portion against a proximal end of the distal pair of lateral shelves in the unguarded position; and
      a bias member connected to the button and at least one of the lower handle portion and the upper handle portion, the bias member providing an upward force on the button when the button is depressed;
   depressing the button;
   sliding the button longitudinally between the distal pair of shelves while the button is depressed to slide the upper handle portion into a guarded position; and
   releasing the button after the button passes a distal end of the distal pair of shelves.

2. The method of claim 1, wherein the button comprises a rounded tab actuated by a user to depress and to slide the button.

3. The method of claim 1, wherein the lower handle portion further comprises a retention stop restricting longitudinal motion of the upper handle portion.

4. The method of claim 1, wherein the lower handle portion comprises a button stop restricting downward movement of the button at a height where the button waist is at a shelf height of the proximal pair of lateral shelves.

5. The method of claim 1, wherein the lower handle portion includes a grip feature extending from a bottom surface of the lower handle portion.

6. The method of claim 1, wherein the lower handle portion further comprises a textured grip surface adjacent to the grip feature.

7. A guarded surgical knife handle comprising:
   a lower handle portion, the lower handle portion comprising:
      a blade holder extending past a distal edge of the lower handle portion adapted to hold a blade;
      a proximal pair of lateral shelves separated by a first lateral spacing;
      a distal pair of lateral shelves separated by a second lateral spacing;
   an upper handle portion, the upper handle portion comprising:
      a guard portion that is open at a distal end of the upper handle portion and sized to surround the blade;
      a proximal post extending downwardly between the proximal pair of shelves and comprising a first widened post portion below the proximal pair of shelves that is wider than the first lateral spacing; and
      a distal post extending downwardly between the distal pair of shelves and comprising a second widened post portion below the distal pair of shelves that is wider than the second lateral spacing;
   a button extending through a button hole in an upper surface of the upper handle portion, the button comprising a button waist narrower than the second lateral spacing and a widened button portion below the button waist wider than the second lateral spacing; and
   a bias member connected to the button and at least one of the lower handle portion and the upper handle portion, the bias member providing an upward force on the button when the button is depressed.

8. The guarded surgical knife handle of claim 1, wherein the guard portion comprises a transparent material.

9. The guarded surgical knife handle of claim 1, wherein the bias member comprises a cantilevered pin.

10. The guarded surgical knife handle of claim 9, wherein the button further comprises a bottom groove, the cantilevered pin fitting within the bottom groove of the button.

11. The guarded surgical knife handle of claim 1, wherein the bias member is connected to the upper handle portion.

12. The guarded surgical knife handle of claim 1, wherein the guard portion comprises an underside configured to fit below the blade when the guard portion is in a guarded position, the underside further configured to contact the distal edge of the lower handle portion when the guard portion is in an unguarded position.

13. The guarded surgical knife handle of claim 12, wherein the underside includes a channel sized to fit around the blade holder.

14. The guarded surgical knife handle of claim 1, wherein the button comprises a rounded tab actuated by a user to depress and to slide the button.

15. The guarded surgical knife handle of claim 1, wherein the widened button portion contacts a proximal end of the distal shelves when the guard portion is in an unguarded position.

16. The guarded surgical knife handle of claim 1, wherein the button is past a distal end of the distal shelves when the guard portion is in a guarded position.

17. The guarded surgical knife handle of claim 1, wherein:
   the lower handle portion comprises an outer portion and an insert portion;
   the blade holder is formed in the outer portion; and
   the proximal pair of lateral shelves and the distal pair of lateral shelves are formed in the insert portion.

18. The guarded surgical knife handle of claim 1, wherein the lower handle portion further comprises a retention stop restricting longitudinal motion of the upper handle portion.

19. The guarded surgical knife handle of claim 1, wherein the bias member is attached to a bias member base on the upper handle portion, and the retention stop interferes with the bias member base to restrict the longitudinal motion of the upper handle portion.

20. The guarded surgical knife handle of claim 1, wherein the lower handle portion comprises a button stop restricting downward movement of the button at a height where the button waist is at a shelf height of the proximal pair of lateral shelves.

21. The guarded surgical knife handle of claim 1, wherein the button includes an alignment feature to prevent rotation of the button.

22. The guarded surgical knife handle of claim 1, wherein the blade holder includes a blade contact stop restricting vertical movement of the guard portion.

23. The guarded surgical knife handle of claim 1, wherein the blade contact stop comprises an upper post fitting between ribs on an inner surface of the guard portion.

24. The guarded surgical knife handle of claim 1, wherein the lower handle portion includes a grip feature extending from a bottom surface of the lower handle portion.

25. The guarded surgical knife handle of claim 24, wherein the grip feature includes a flattened bottom surface preventing the guarded surgical knife handle from rolling when placed on a flat surface.

26. The guarded surgical knife handle of claim 24, wherein the lower handle portion further comprises a textured grip surface adjacent to the grip feature.

* * * * *